(12) United States Patent
Inoue et al.

(10) Patent No.: US 8,693,759 B2
(45) Date of Patent: Apr. 8, 2014

(54) IMAGE PROCESSING DEVICE AND IMAGE PROCESSING METHOD

(75) Inventors: Atsushi Inoue, Tokyo (JP); Tomohiro Nagao, Tokyo (JP)

(73) Assignee: Hitachi Medical Corporation, Tokyo (JP)

( * ) Notice: Subject to any disclaimer, the term of this patent is extended or adjusted under 35 U.S.C. 154(b) by 251 days.

(21) Appl. No.: 13/128,567

(22) PCT Filed: Nov. 10, 2009

(86) PCT No.: PCT/JP2009/069078
§ 371 (c)(1),
(2), (4) Date: May 10, 2011

(87) PCT Pub. No.: WO2010/055817
PCT Pub. Date: May 20, 2010

(65) Prior Publication Data
US 2011/0221756 A1    Sep. 15, 2011

(30) Foreign Application Priority Data
Nov. 13, 2008 (JP) .................................. 2008-290892

(51) Int. Cl.
*G06K 9/00* (2006.01)
(52) U.S. Cl.
USPC ........................................................ 382/131
(58) Field of Classification Search
USPC ........................................................ 382/131
See application file for complete search history.

(56) References Cited

U.S. PATENT DOCUMENTS

| 2004/0220466 | A1  | 11/2004 | Matsumoto |
| 2005/0020878 | A1* | 1/2005  | Ohnishi et al. ................. 600/117 |
| 2006/0280347 | A1* | 12/2006 | Shirahata et al. ............. 382/128 |
| 2007/0064982 | A1  | 3/2007  | Licato et al. |
| 2007/0116342 | A1* | 5/2007  | Zarkh et al. ................... 382/130 |
| 2009/0010519 | A1* | 1/2009  | Wakai et al. .................. 382/131 |
| 2009/0016483 | A1* | 1/2009  | Kawasaki et al. ................ 378/4 |

FOREIGN PATENT DOCUMENTS

| JP | 2004-313736 | 11/2004 |
| JP | 2006-20874  | 1/2006  |
| JP | 2007-83030  | 4/2007  |

OTHER PUBLICATIONS

International Search Report in PCT/JP2009/069078.

* cited by examiner

*Primary Examiner* — Kee M Tung
*Assistant Examiner* — Nicholas R Wilson
(74) *Attorney, Agent, or Firm* — Cooper & Dunham LLP

(57) ABSTRACT

Provided is an image processing device capable of effectively displaying the details of a plurality of different branches included in a structure that is divided into a plurality of branches. An image processing device 100 reads the entire image of a coronary artery region, extracts a coronary artery region A from the read image data, displays the coronary artery region A, calculates cores 41, 42, and 43 of three coronary arteries A1, A2, and A3, and calculates the lengths of blood vessels. In addition, when an operator uses a GUI 33 that is displayed in parallel to the entire image of the coronary artery region A to designate an arbitrary scale position on the GUI 33, a CPU 101 calculates positions on the blood vessels A1, A2, and A3 corresponding to the designated scale position. The CPU 101 displays vertical tomographic images 321, 322, and 323 at the calculated corresponding positions in a detailed image display region 32.

8 Claims, 17 Drawing Sheets

IMAGE PROCESSING DEVICE AND IMAGE PROCESSING METHOD

TECHNICAL FIELD

The present invention relates to an image processing device that displays a structure divided into a plurality of branches such as coronary arteries.

BACKGROUND ART

For example, the tomographic images of an examinee captured by an X-ray CT (Computed Tomography) apparatus or an MRI (Magnetic Resonance Imaging) apparatus have been known as images used for medical diagnosis. It is possible to stack a plurality of tomographic images to generate a three-dimensional volume image and display the three-dimensional volume image. In addition, it is possible to perform image processing and display an appropriate image, for example, a CPR (Curved Planar Reconstruction) image, an MIP (Maximum Intensity Projection) image or the like.

For example, Patent Document 1 or Patent Document 2 discloses an image processing device in which, when an operator selects any one of coronary arteries in an image of the coronary arteries in a heart region and designates a position on the selected coronary artery, a vertical tomographic image of the selected coronary artery at the designated position or a plurality of tomograms before and after the coronary artery including the designated position is displayed.

PRIOR ART DOCUMENT

Patent Document

Patent Document 1: JP-A-2004-283373
Patent Document 2: JP-A-2001-175847

SUMMARY OF THE INVENTION

Problem to be Solved by the Invention

However, in the above-mentioned Patent Document 1 or Patent Document 2, a plurality of tomograms before and after only a blood vessel including the designated position is displayed. Therefore, when coronary arteries other than the selected coronary artery are observed, it is necessary to select the coronary arteries again. As a result, it takes a lot of time and effort to perform the operation and it takes a long time to observe all of the coronary arteries.

The invention has been made in view of the above-mentioned problems and an object of the invention is to provide an image processing device capable of effectively displaying the details of a plurality of different branches included in a structure that is divided into a plurality of branches.

Means of Solving the Problem

In order to achieve the object, according to an aspect of the invention, an image processing device includes: display region forming means configured to form a first region in which the entire image of a structure divided into a plurality of branches is displayed and a second region in which detailed images of the plurality of different branches included in the entire image are displayed on the same display screen; designating configured to designate a position of each branch to be displayed in the second region on the basis of the entire image displayed in the first region; and display means configured to form the detailed image of each branch to be displayed on the basis of the position designated by the designating means and displaying each detailed image in the second region.

The image processing device according to the above-mentioned aspect may further include GUI display means configured to generate a GUI for designating the position of the branch in a length direction and displaying the GUI. When the GUI generated by the GUI display means is operated to designate an arbitrary position on the GUI, the designating means may calculate a position on each branch to be displayed which corresponds to the designated position on the GUI. The display means may display the detailed image of each branch at the position calculated by the designating means in the second region.

When a pointer displayed on the entire image is operated to input an instruction to designate an arbitrary position on any branch in the entire image, the designating means may calculate positions, which correspond to the position designated by the input instruction, on branches other than the branch designated by the input instruction among the branches to be displayed. The display means may display the detailed image of each branch at the position designated by the input instruction or the positions calculated by the designating means in the second region.

The detailed image displayed in the second region may be a tomographic image orthogonal to a core of each branch or a three-dimensional perspective projection image.

The image processing device according to the above-mentioned aspect may further include detecting means configured to detect an abnormal part on the basis of the detailed image. The display means may display the detailed image from which the abnormal part is detected by the detecting means so as to be emphasized.

The display means may display the detailed image in the second region such that the size of the detailed image of a main branch or a part of the branch close to a branch portion is larger than that of a lateral branch or apart of the branch close to a leading end.

When the entire image displayed in the first region includes three coronary arteries, at least the three coronary arteries may be display targets in the second region.

According to another aspect of the invention, an image processing method includes: a display region forming step of forming a first region in which the entire image of a structure divided into a plurality of branches is displayed and a second region in which detailed images of the plurality of different branches included in the entire image are displayed on the same display screen; a designating step of designating a position of each branch to be displayed in the second region on the basis of the entire image displayed in the first region; and a display step of forming the detailed image of each branch to be displayed on the basis of the position designated by the designating step and displaying each detailed image in the second region.

Effect of the Invention

According to the invention, it is possible to provide an image processing device capable of effectively displaying the details of a plurality of different branches included in a structure that is divided into a plurality of branches.

MODES FOR CARRYING OUT THE INVENTION

Hereinafter, exemplary embodiments of the invention will be described in detail with reference to the accompanying drawings.

A coronary artery in a heart region will be described below as an example of a structure which is to be displayed by an image processing device according to the invention and is divided into a plurality of branches. The coronary arteries of the heart have a structure in which an aorta is divided at a branch portion into three main branches and lateral branches. The three main branches of the coronary arteries are a right coronary artery that extends to the right side of the heart, a left anterior descending coronary artery that extends to the front left side of the heart, and a left circumflex coronary artery that extends to the rear left side of the heart. In the following description, the three main branches mean three coronary arteries. Blood vessels other then the three coronary arteries are referred to as the lateral branches.

For example, blood vessels, bronchi, and nerves in the lung region are given as examples other than the structure that is divided into a plurality of branches.

First Embodiment

First, the structure of an image process system 1 to which the image processing device according to the invention is applied will be described below.

Figure 1:
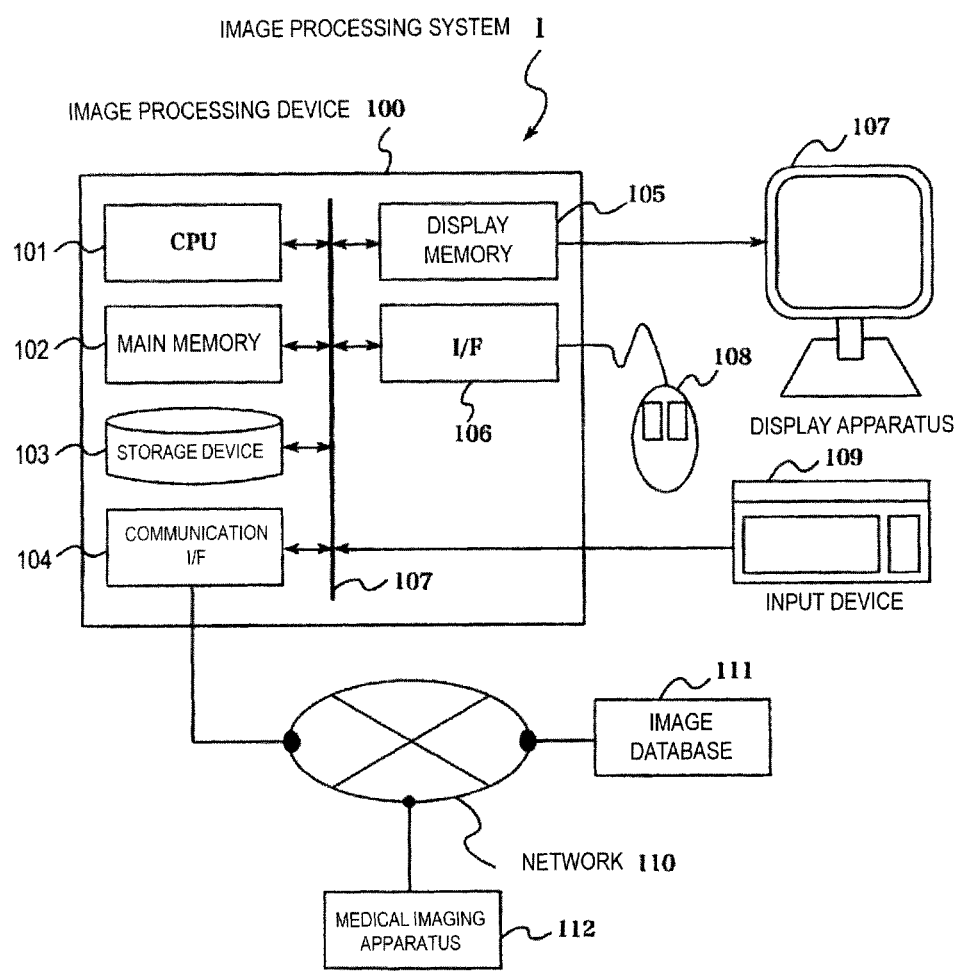
FIG. 1 is a hardware structure diagram illustrating the overall structure of an image process system 1.

As shown in FIG. 1, the image process system 1 includes an image processing device 100 having a display apparatus 107 and an input device 109, and an image database 111 and a medical imaging apparatus 112 that are connected to the image processing device 100 through a network 110.

The image processing device 100 is, for example, a computer for image diagnosis that is provided in a hospital or the like.

The image processing device 100 includes a CPU (Central Processing Unit) 101, a main memory 102, a storage device 103, a communication interface (communication I/F) 104, a display memory 105, and an interface (I/F) 106 for connection to an external apparatus, such as a mouse 108, which are connected to each other by a bus 107.

The CPU 101 calls a program that is stored in, for example, the main memory 102 or the storage device 103 to a work memory area on a RAM of the main memory 102, executes the program, controls driving of each unit connected thereto through the bus 107, and implements various kinds of processes performed by the image processing device 100.

In addition, in the first to sixth embodiments, the CPU 101 performs the following processes (image display processes (1) to (6)) related to a display of images. In the image display processes (1) to (6), the CPU 101 forms an entire image display region 31 for displaying the entire image of the coronary arteries and a detailed image display region 32 for displaying detailed images of the three coronary arteries or lateral branches on a display screen of the display apparatus 107 (see FIG. 3). When the mouse 108 or the input device 109 is operated to designate a position on the entire image displayed in the entire image display region 31, the CPU 101 calculates a corresponding position on each blood vessel whose detailed image will be displayed, on the basis of the designated position, and displays the detailed image of each blood vessel at the designated position or the corresponding position in the detailed image display region 32.

The main memory 102 includes, for example, a ROM (Read Only Memory) and a RAM (Random Access Memory). The ROM permanently stores, for example, programs, such as a boot program and a BIOS of the computer, and data. The RAM temporarily stores the program and data loaded from, for example, the ROM and the storage device 103 and has a work area used by the CPU 101 to perform various kinds of processes.

The storage device 103 is for reading or writing data from or to a HDD (Hard Disk Drive) or other recording media and stores, for example, the programs executed by the CPU 101, data required for executing the programs, and an OS (operating system). As the programs, a control program corresponding to the OS or application programs are stored. These program codes are read by the CPU 101 if necessary, are transmitted to the RAM of the main memory 102, and are then executed as various kinds of means.

The communication I/F 104 includes, for example, a communication control device and a communication port and performs communication between the image processing device 100 and the network 110. The communication I/F 104 controls communication with the image database 111, another computer, or the medical imaging apparatus 112, such as an X-ray CT apparatus or an MRI apparatus, through the network 110.

The I/F 106 is a port for connecting peripheral devices and performs data communication with the peripheral devices. For example, an input device, such as the mouse 108, may be connected to the image processing device through the I/F 106. The mouse 108 includes left and right switch buttons and a mouse wheel 108a.

The display memory 105 is a buffer that temporarily stores display data input from the CPU 101. The stored display data is output to the display apparatus 107 at a predetermined timing.

The display apparatus 107 includes a display device, such as a liquid crystal panel or a CRT monitor, and a logic circuit that performs a display process in cooperation with the display device, and is connected to the CPU 101 through the display memory 105. The display apparatus 107 displays the display data stored in the display memory 105 on the display device under the control of the CPU 101.

The input device 109 is, for example, various kinds of switches or a keyboard and outputs various kinds of instructions or information input by an operator to the CPU 101. The operator uses external apparatuses, such as the display apparatus 107, the input device 109, and the mouse 108, to interactively operate the image processing device 100.

The network 110 includes various kinds of communication networks, such as a LAN (Local Area Network), a WAN (Wide Area Network), an Intranet, and the Internet, and mediates communication connection between the image database 111, a server, or other information apparatuses and the image processing device 100.

The image database 111 accumulates and stores medical images captured by the medical imaging apparatus 112 that captures images used for medical diagnosis, such as the X-ray CT apparatus or the MRI apparatus, and is provided in, for example, a server of a hospital or a medical center. In the image process system 1 shown in FIG. 1, the image database 111 is connected to the image processing device 100 through the network 110. However, the image database 111 may be provided in, for example, the storage device 103 of the image processing device 100.

Next, the operation of the image processing system 100 according to the first embodiment will be described with reference to FIGS. 2 to 5.

The CPU 101 of the image processing device 100 reads a program and data related to an image display process (1) from the main memory 102 and performs the image display process (1) on the basis of the program and data.

Figure 2:
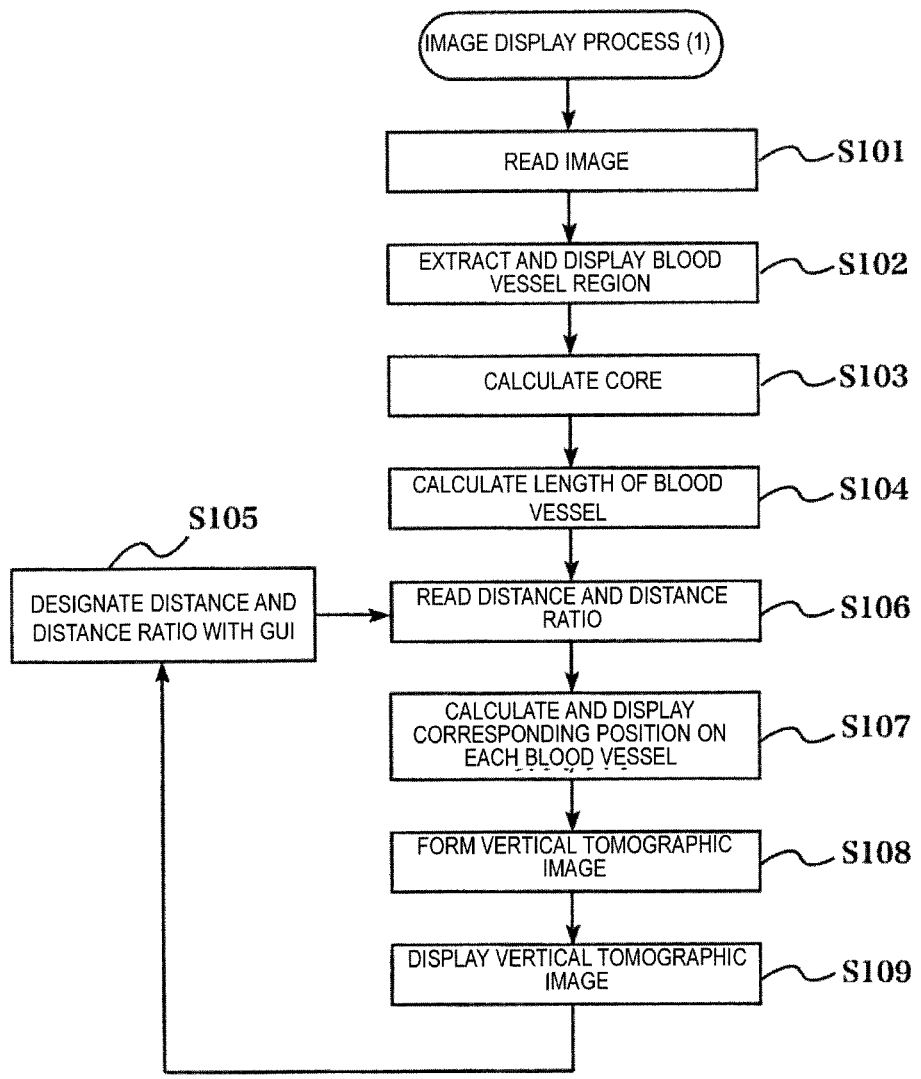
FIG. 2 is a flowchart illustrating a flow of an image display process (1) according to a first embodiment.

In the image display process (1) shown in FIG. 2, first, the CPU 101 of the image processing device 100 performs a process of reading image data (Step S101). The CPU 101 reads three-dimensional image data that is captured in a range of a heart region by the medical imaging apparatus 112 from the image database 111 or the storage device 103.

Then, the CPU 101 extracts a coronary artery region A from the acquired three-dimensional image data and displays the coronary artery region A in the entire image display region 31 of the display apparatus 107 (Step S102).

Figure 3:
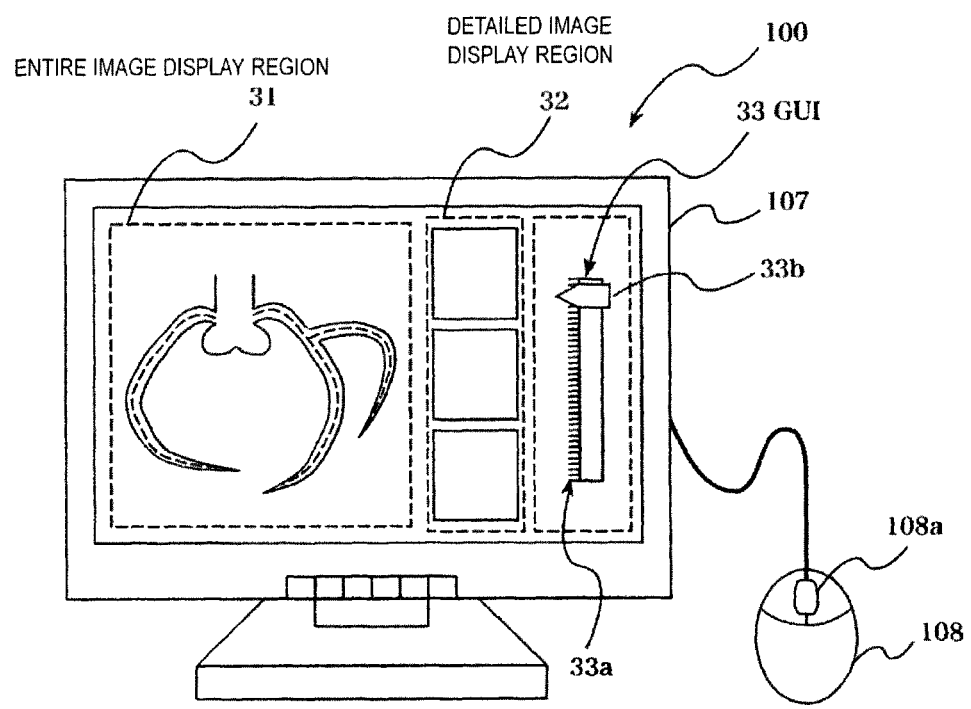
FIG. 3 is a diagram illustrating an example of a display of an image processing device 100.

As shown in FIG. 3, the display apparatus 107 includes the entire image display region 31 for displaying the entire image of the coronary artery region A and the detailed image display region 32 for displaying each of the detailed images (for example, vertical tomographic images) of the three coronary arteries. In the first embodiment, a GUI 33, which will be described below, for inputting a position on the coronary arteries is displayed.

The CPU 101 forms, for example, a volume rendering image and CPR (Carved Planar Reconstruction) images or MIP (Maximum Intensity Projection) images of three coronary arteries A1, A2, and A3, as the entire image of the coronary artery region A and displays the formed image in the entire image display region 31.

Figure 4:
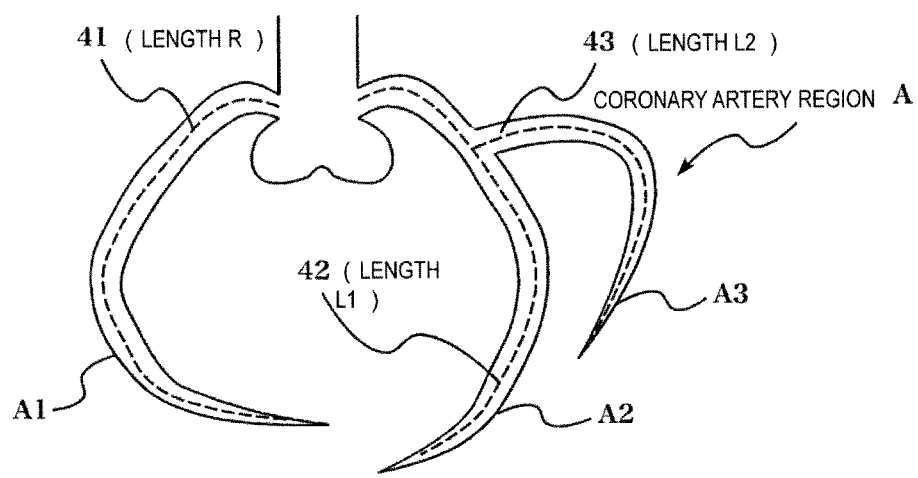
FIG. 4 is a diagram illustrating an extraction of cores from coronary arteries and a calculation of lengths of the cores.

Then, as shown in FIG. 4, the CPU 101 calculates a core passing through the vicinity of the center of each of the coronary arteries (hereinafter, also referred to as blood vessels) A1, A2, and A3 from the coronary artery region A and acquires a core 41 of the right coronary artery A1, a core 42 of the left anterior descending coronary artery A2, and a core 43 of the left circumflex coronary artery A3 (Step S103 of FIG. 2). In addition, the CPU 101 calculates a length of each blood vessel from the branch portion to the deepest portion for the acquired cores 41, 42, and 43 (Step S104). For a length R of the core 41 of the right coronary artery A1 and a length L1 of the core 42 of the left anterior descending coronary artery A2, the branch portion of the aorta is a starting point. For a length L2 of the core 43 of the left circumflex coronary artery A3, a branch point from the left anterior descending coronary artery A2 is the starting point.

The CPU 101 normalizes the calculated lengths R, L1, and L2 of the blood vessels. The normalization is to calculate a distance ratio of the lengths of the blood vessels with any of the lengths R, L1, and L2 of the blood vessels as a reference. After normalizing the lengths R, L1, and L2 of the blood vessels, the CPU 101 associates the GUI 33 displayed on the display apparatus 107 with the mouse wheel 108a.

Next, the GUI (Graphical User Interface) 33 (object) will be described below.

Figure 5:
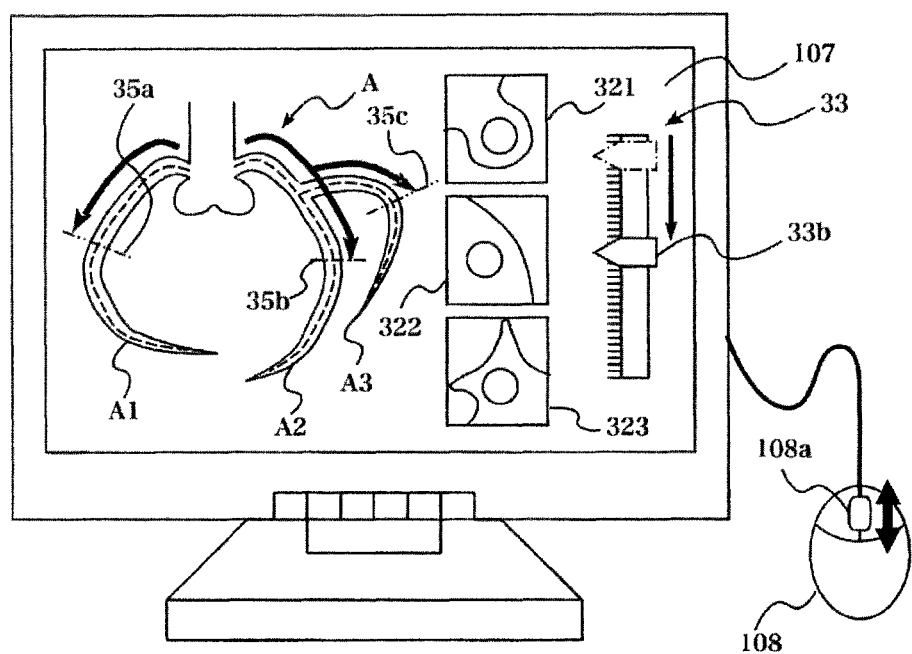
FIG. 5 is a diagram illustrating a blood vessel designating operation of the image processing device 100 and a display example corresponding to the blood vessel designating operation.

As shown in FIGS. 3 and 5, the GUI 33 is displayed in parallel to the entire image display region 31 of the display apparatus 107. The GUI 33 includes a scale 33a that is associated with the length (length direction) of any one of the blood vessels A1, A2, and A3 and a slider 33b that designates a scale position. The slider 33b is moved and displayed on the scale 33a in the vertical direction in operative association with the rotation of the mouse wheel 108a. For example, the uppermost portion of the scale 33a of the GUI 33 is associated with the starting point (the branch portion of the aorta or the branch portion from the left anterior descending coronary artery) of a reference blood vessel and the lowermost portion thereof is associated with the deepest portion of the reference blood vessel.

Then, in Step S105 of FIG. 2, when the operator operates the mouse wheel 108a to move the slider 33b of the GUI 33 and designate an arbitrary scale position on the GUI 33 (Step S105), the CPU 101 reads a position (a distance from the starting point or the distance ratio) on the coronary artery region A corresponding to the position designated by the GUI 33 (Step S106). That is, since the scale of the GUI 33 is associated with the position of any one (for example, A1) of the blood vessels A1, A2, and A3 in the length direction, a position on the associated blood vessel is read.

Then, the CPU 101 calculates corresponding positions on the other blood vessels (for example, A2 and A3) from the distance or the distance ratio read in Step S106. In addition, the CPU 101 displays lines 35a, 35b, and 35c indicating designated positions on the blood vessels A1, A2, and A3 of the coronary artery region A displayed in the entire image display region 31, respectively (Step S107; see FIG. 5).

Further, the CPU 101 forms vertical tomographic images 321, 322, and 323 of the blood vessels A1, A2, and A3 at the designated position and the corresponding positions, respectively, and displays the vertical tomographic images 321, 322, and 323 in the detailed image display region 32 (Steps S108 and 109).

FIG. 5 shows a display state of the display apparatus 107 of the image processing device 100 at this stage.

As shown in FIG. 5, when the slider 33b of the GUI 33 is moved to an arbitrary scale position by the operation of the mouse wheel 108a and the position is designated, positions on the blood vessels A1, A2, and A3 of the coronary artery region A corresponding to the designated position are calculated, and the lines 35a, 35b, and 35c are displayed at the corresponding positions. In addition, the vertical tomographic images 321, 322, and 323 of the blood vessels A1, A2, and A3 at the corresponding positions are formed and displayed in the detailed image display region 32.

Then, in the process from Step S105 to Step S109, whenever the GUI 33 is used to perform position designating operation, the vertical tomographic images 321, 322, and 323 are formed at the positions on the blood vessels A1, A2, and A3 corresponding to the designated position and are then displayed.

As described above, the image processing device 100 according to the first embodiment extracts the coronary artery region A from the read image data, displays the coronary artery region A, calculates the cores 41, 42, and 43 of the three coronary arteries A1, A2, and A3, and calculates the lengths of the three coronary arteries. In addition, when the GUI 33 that is associated with the positions of the blood vessels (three coronary arteries) in the length direction and designates the positions on the blood vessels is used to designate an arbitrary position of the blood vessel, the CPU 101 calculates a corresponding position on each of the blood vessels A1, A2, and A3 on the basis of the designated position and displays the vertical tomographic images 321, 322, and 323 at the calculated corresponding positions in the detailed image display region 32.

Therefore, it is possible to display the vertical tomographic images of a plurality of different blood vessels (in this embodiment, three coronary arteries) at the corresponding positions in the length direction on the same display screen with an easy operation and thus effectively observe the coronary artery region. In addition, since the GUI 33 is used to collectively designate the positions of the blood vessels in a detailed image, it is easy to operate. Further, the use of the GUI 33 makes it possible to perform the position designating operation in operative association with the rotation of the mouse wheel 108a. Therefore, it is possible to continuously and smoothly observe each detailed image from an upstream portion to a downstream portion of each blood vessel.

Second Embodiment

Next, an image process system 1 according to a second embodiment will be described below. The hardware structure of the image process system 1 according to the second embodiment is the same as that of the image process system 1 according to the first embodiment shown in FIG. 1 and thus a description thereof will be omitted. In the second embodiment, the same components as those in the first embodiment are denoted by the same reference numerals.

Figure 6:
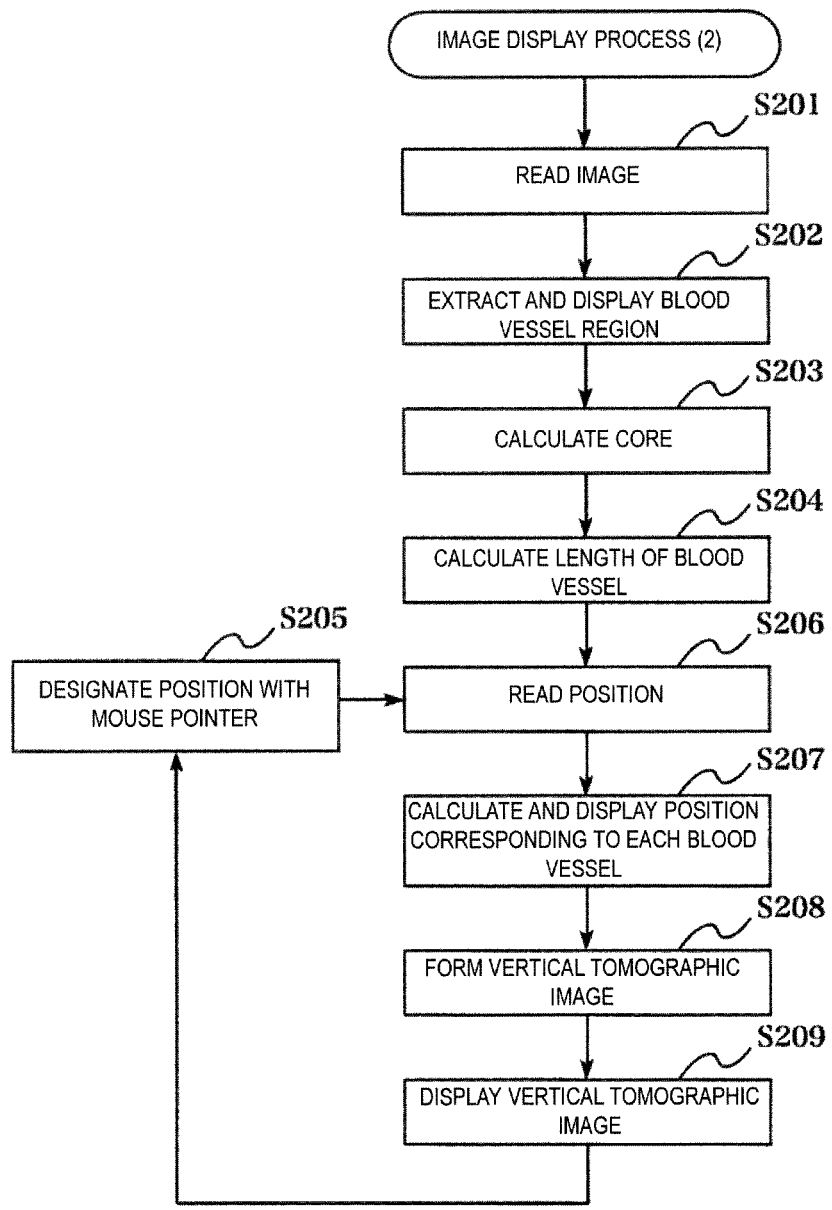
FIG. 6 is a flowchart illustrating a flow of an image display process (2) according to a second embodiment.

In the second embodiment, the CPU 101 performs an image display process (2) shown in FIG. 6. In the image display process (2), when a pointer displayed on a display screen is operated to designate any one of the blood vessels in the coronary artery region A, the CPU 101 calculates positions on the other blood vessels corresponding to the designated position, forms vertical tomographic images at the designated positions, and displays the vertical tomographic images.

Next, the operation of the image processing device 100 according to the second embodiment will be described with reference to FIGS. 6 to 8.

The CPU 101 of the image processing device 100 according to the second embodiment reads a program and data related to the image display process (2) shown in FIG. 6 from the main memory 102 and performs the image display process (2) on the basis of the program and data.

In the image display process (2) shown in FIG. 6, first, the CPU 101 of the image processing device 100 reads three-dimensional image data from the storage device 103, similarly to the process from Step S101 to Step S104 in the first embodiment (Step S201). Then, the CPU 101 extracts the coronary artery region A from the acquired three-dimensional image data and displays the coronary artery region A in the entire image display region 31 of the display apparatus 107 (Step S202). In addition, the CPU 101 calculates the cores 41, 42, and 43 passing through the vicinities of the centers of the blood vessels A1, A2, and A3 from the coronary artery region A (Step S203). Then, the CPU 101 calculates the lengths R, L1, and L2 of the blood vessels from a branch portion to the deepest portion for the acquired cores 41, 42, and 43 and normalizes the calculated lengths R, L1, and L2 of the blood vessels (Step S204).

The CPU 101 displays a mouse pointer 36 that is moved in operative association with the movement of the mouse 108 on the display screen.

In Step S205 of FIG. 6, when the operator operates the mouse 108 to designate an arbitrary position of any one of the blood vessels with the mouse pointer 36 (Step S205), the CPU 101 reads information of the designated position (Step S206). In addition, the CPU 101 calculates corresponding positions of the blood vessels other than the designated blood vessel on the basis of the information of the designated position. Then, the CPU 101 displays the lines 35a, 35b, and 35c indicating the designated position and the corresponding positions on the blood vessels A1, A2, and A3 of the coronary artery region A displayed in the entire image display region 31, respectively (Step S207).

Figure 7:
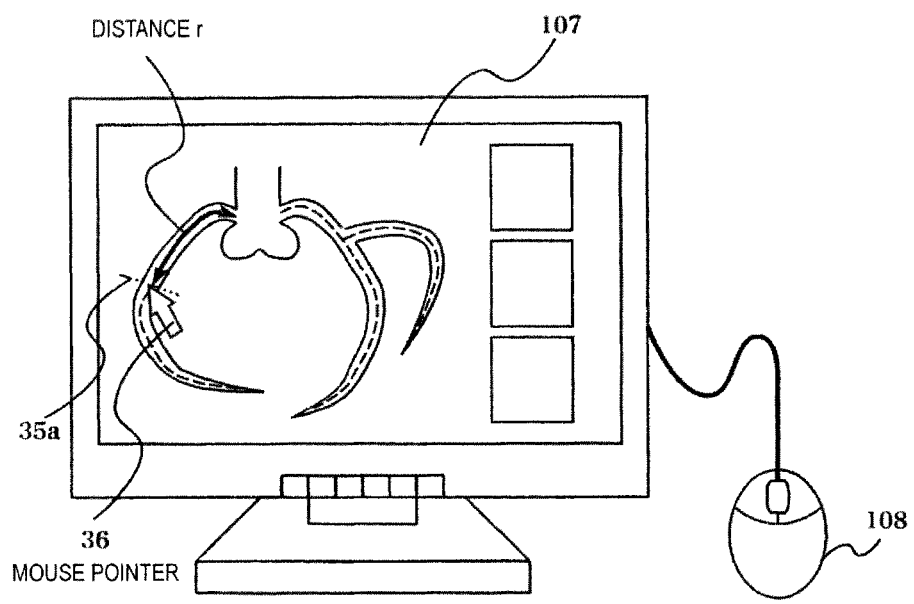
FIG. 7 is a diagram illustrating an operation of designating a position on a blood vessel according to the second embodiment.

For example, as shown in FIG. 7, when the operator uses the mouse pointer 36 to designate an arbitrary position on the blood vessel A1, the CPU 101 calculates a distance r between the designated position and the starting point (branch portion) of the blood vessel. In addition, the CPU 101 determines corresponding positions on the other coronary arteries A2 and A3 on the basis of the distance r and the length R from the branch portion to the deepest portion of the blood vessel which is calculated in Step S204.

The corresponding positions of the other blood vessels have the same length on the core as the length r or have the same distance ratio.

When the corresponding positions have the same distance r, a length from the starting point of the core of each of the blood vessels A2 and A3 to the corresponding position is r.

When the corresponding positions have the same distance ratio, a distance ratio rateR of the distance r to the length R of the designated blood vessel is calculated by the following Expression (1) and the lengths of the other blood vessels A2 and A3 are multiplied by the distance ratio rateR.

$$\text{rate}R = r/R. \quad \text{[Expression (1)]}$$

That is, the lengths L1 and L2 of the blood vessels A2 and A3 are multiplied by the distance ratio rateR to calculate distances l1 and l2, and positions that are the distances l1 and l2 away from the branch portions on the cores are the corresponding positions.

The CPU 101 forms the vertical tomographic images of the blood vessels A1, A2, and A3 at the designated position or the corresponding positions and displays the vertical tomographic images in the detailed image display region 32 (Steps S208 and 209).

Figure 8:
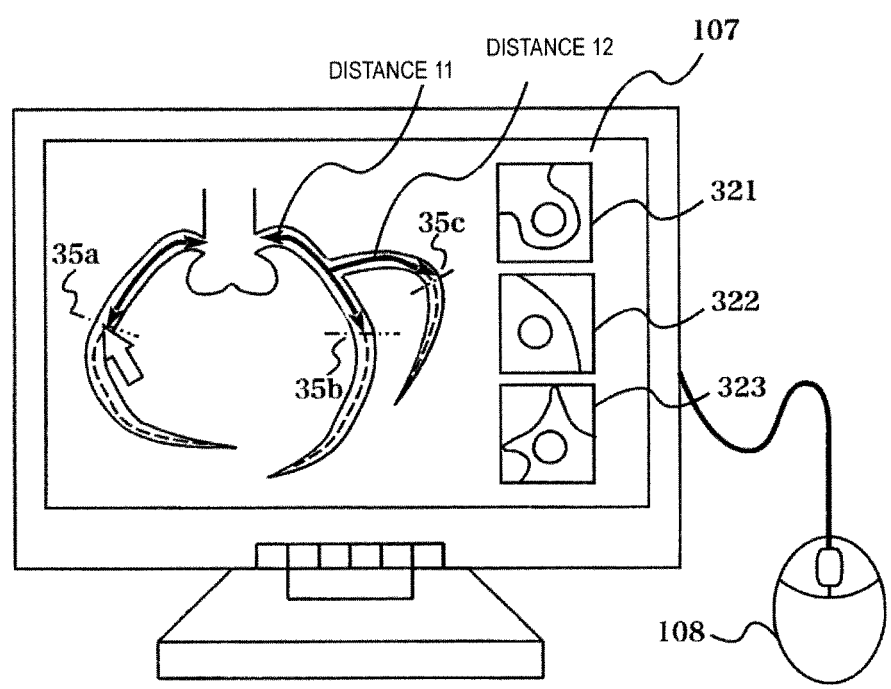
FIG. 8 is a diagram illustrating a display example according to the second embodiment.

FIG. 8 shows a display state of the display apparatus 107 of the image processing device 100 at this stage.

As shown in FIG. 8, when the mouse pointer 36 is operated to designate an arbitrary position on, for example, the blood vessel A1, positions on the other blood vessels A2 and A3 of the coronary artery region A corresponding to the designated position are calculated, and the lines 35a, 35b, and 35c are displayed at the corresponding positions and the designated position. In addition, the vertical tomographic images 321, 322, and 323 of the blood vessels A1, A2, and A3 at the designated position and the corresponding positions are formed and displayed in the detailed image display region 32.

Then, in the process from Step S205 to Step S209, whenever the mouse pointer 36 is operated to designate an arbitrary position of any one of the blood vessels, positions (the corresponding positions) on the other blood vessels corresponding to the designated position are calculated and the vertical tomographic images 321, 322, and 323 at the designated position and the corresponding positions are formed and displayed.

As described above, in the image processing device 100 according to the second embodiment, when the mouse is operated to designate an arbitrary position of any one of the blood vessels, the CPU 101 calculates positions on the other blood vessels corresponding to the designated position, forms vertical tomographic images at the designated position and the calculated corresponding positions, and displays the vertical tomographic images in the detailed image display region 32.

Therefore, the operator simply designates a desired position on a desired coronary artery with the mouse 108 to check vertical tomographic images of the other coronary arteries at corresponding positions as well as a vertical tomographic image at the designated position. Therefore, the operator can effectively observe the coronary arteries with a simple operation.

In the second embodiment, as an example, a position on the blood vessel A1 is designated and positions on the other blood vessels A2 and A3 corresponding to the designated position are calculated. However, a position on the blood vessel A2 may be designated and positions on the other blood vessels A1 and A3 corresponding to the designated position may be calculated, or a position on the blood vessel A3 may be designated and positions on the other blood vessels A1 and A2 corresponding to the designated position may be calculated.

In this case, the following Expressions (2) and (3) correspond to Expression (1) that calculates the distance ratio with respect to the blood vessel length at the designated position. When an arbitrary position on the blood vessel A2 is designated, rate$L1$ is applied, and when an arbitrary position on the blood vessel A3 is designated, rate$L2$ is applied.

$$\text{rate}L1 = r/L1 \quad \text{[Expression (2)]}$$

$$\text{rate}L2 = r/L2 \quad \text{[Expression (3)]}$$

Third Embodiment

Next, an image process system 1 according to a third embodiment will be described. The hardware structure of the image process system 1 according to the third embodiment is the same as that of the image process system 1 according to the first embodiment shown in FIG. 1 and thus a description thereof will be omitted. In the third embodiment, the same components as those in the first embodiment are denoted by the same reference numerals.

Figure 9:
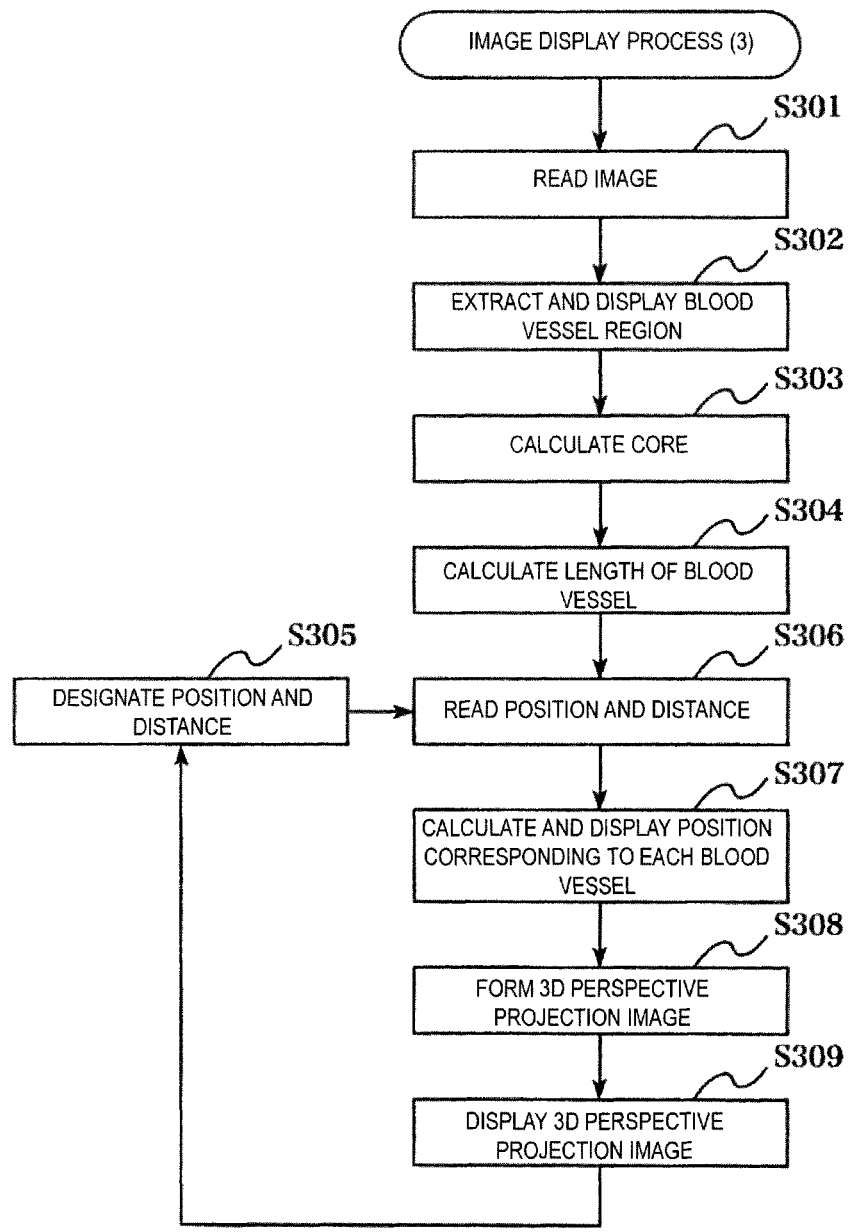
FIG. 9 is a flowchart illustrating a flow of an image display process (3) according to a third embodiment.

In the third embodiment, the CPU 101 performs an image display process (3) shown in FIG. 9. When the GUI 33 or the mouse pointer 36 is operated to designate a position on the blood vessel in the coronary artery region A, the CPU 101 calculates the designated position or corresponding positions on each blood vessel, forms a 3D perspective projection image including these positions, and displays the 3D perspective projection image.

Next, the operation of the image processing device 100 according to the third embodiment will be described with reference to FIGS. 9 and 10.

The CPU 101 of the image processing device 100 according to the third embodiment reads a program and data related to the image display process (3) shown in FIG. 9 from the main memory 102 and performs the image display process (3) on the basis of the program and data.

In the image display process (3), first, the CPU 101 of the image processing device 100 reads three-dimensional image data from the storage device 103, similarly to the process from Step S101 to Step S104 of the first embodiment (Step S301). Then, the CPU 101 extracts the coronary artery region A from the acquired three-dimensional image data and displays the coronary artery region A in the entire image display region 31 of the display apparatus 107 (Step S302). In addition, the CPU 101 calculates the cores 41, 42, and 43 passing through the vicinities of the centers of the blood vessels A1, A2, and A3 from the coronary artery region A (Step S303). Then, the CPU 101 calculates the lengths R, L1, and L2 of the blood vessels from a branch portion to the deepest portion for the acquired cores 41, 42, and 43 and normalizes the calculated lengths R, L1, and L2 of the blood vessels (Step S304).

In Step S305 of FIG. 9, when the operator operates the mouse 108 to designate a position on the blood vessel or a distance from a starting position with, for example, the GUI 33 described in the first embodiment or the mouse pointer 36 described in the second embodiment (Step S305), the CPU 101 reads information of the designated position and distance (Step S306). In addition, the CPU 101 calculates corresponding positions of all of the blood vessels A1, A2, and A3 on the basis of the information of the designated position and distance. Then, the CPU 101 displays the lines 35a, 35b, and 35c indicating the designated position and the corresponding positions on the blood vessels A1, A2, and A3 of the coronary artery region A displayed in the entire image display region 31, respectively (Step S307). The designated position or the corresponding positions are calculated by the same method as that in the first embodiment or the second embodiment and thus a description thereof will be omitted.

The CPU 101 forms 3D perspective projection images of regions including the designated position and the corresponding positions on the blood vessels A1, A2, and A3 and displays the 3D perspective projection images in the detailed image display region 32 (Steps S308 and 309). The 3D perspective projection image is an image of the blood vessel projected onto a flat projection plane, when viewed from a virtual point of view set in the blood vessel in a direction within a given range as a viewing angle, and is also referred to as a virtual endoscopic image.

For example, a position of the point of view or a direction of the viewing angle of the 3D perspective projection image may be set to any position or any direction as long as the designated position and the corresponding positions of the blood vessels A1, A2, and A3 are included in the image.

Figure 10:
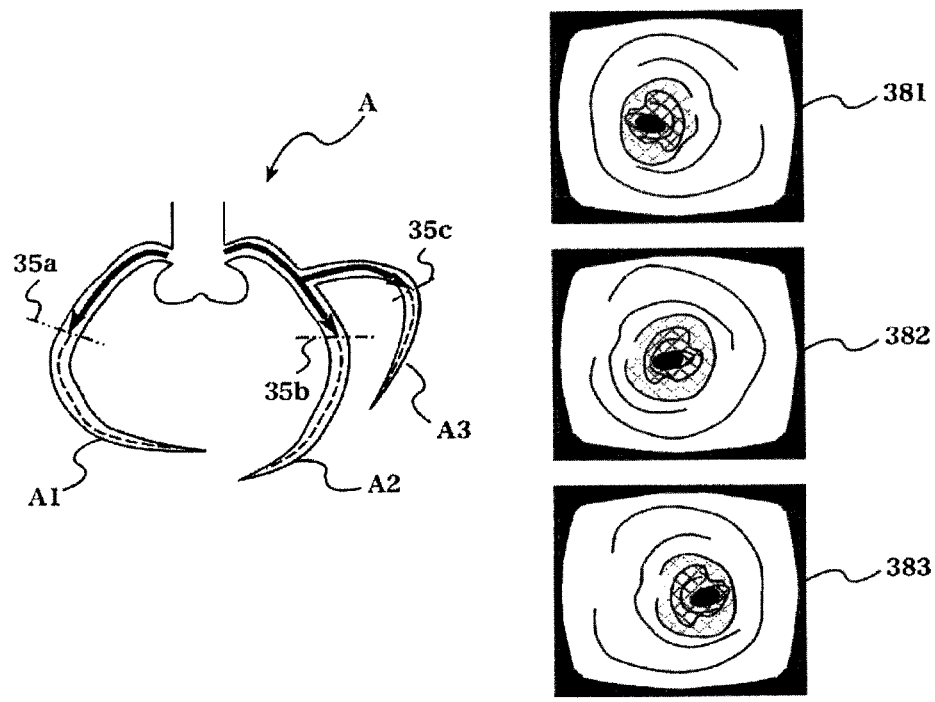
FIG. 10 is a diagram illustrating a display example according to the third embodiment.

FIG. 10 shows a display state of the display apparatus 107 of the image processing device 100 at this stage.

As shown in FIG. 10, when an arbitrary position on the blood vessel or the distance from the starting point is designated, positions on the blood vessels A1, A2, and A3 of the coronary artery region A corresponding to the designated position or distance are calculated and the lines 35a, 35b, and 35c are displayed at the corresponding positions and the designated position. In addition, 3D perspective projection images 381, 382, and 383 of the blood vessels A1, A2, and A3 at the corresponding positions and the designated position are formed and displayed in the detailed image display region 32.

In the process from Step S305 to Step S309, whenever an arbitrary position on a blood vessel is designated, positions (corresponding positions) on the other blood vessels corresponding to the designated position are calculated, and the 3D perspective projection images 381, 382, and 383 at the designated position and the corresponding positions are formed and displayed.

As described above, in the image processing device 100 according to the third embodiment, when the GUI 33 or the mouse pointer 36 is operated to designate arbitrary positions on a plurality of displayed blood vessels or the distance from the starting point, the CPU 101 calculates a position on each blood vessel corresponding to the designated position, forms the 3D perspective projection images at the designated positions and the calculated corresponding positions, and displays the 3D perspective projection images in the detailed image display region 32.

Therefore, the operator can simultaneously check the 3D perspective projection images at the positions on all of the coronary arteries which correspond to the designated position on the coronary artery and have the same distance or the same distance ratio as the designated position. Therefore, it is possible to display the 3D perspective projection images of the three coronary arteries at the corresponding positions on the same display screen with a simple operation and effectively observe images in the depth direction that are not displayed in the vertical tomographic image.

Fourth Embodiment

Next, an image process system 1 according to a fourth embodiment will be described. The hardware structure of the image process system 1 according to the fourth embodiment is the same as that of the image process system 1 according to the first embodiment shown in FIG. 1 and thus a description thereof will be omitted. In the fourth embodiment, the same components as those in the first embodiment are denoted by the same reference numerals.

Figure 11:
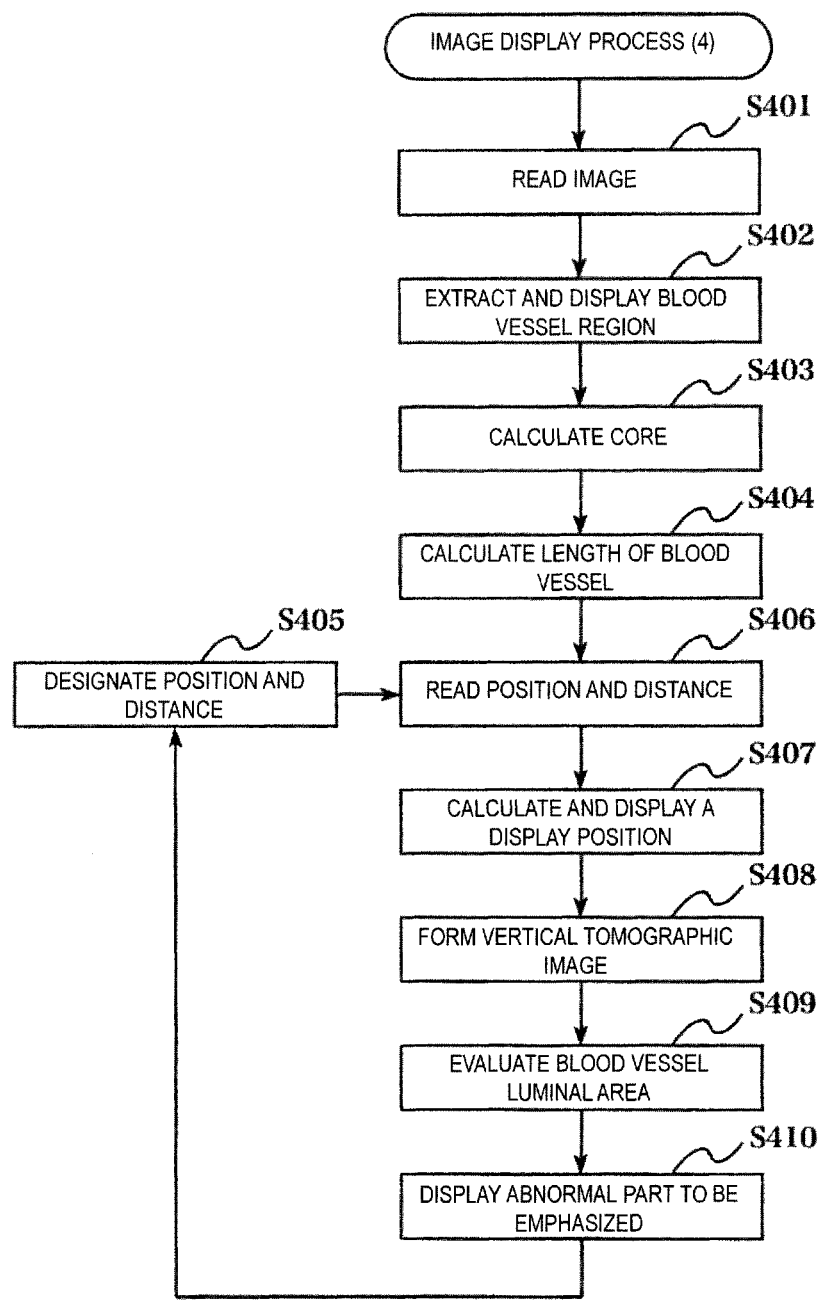
FIG. 11 is a flowchart illustrating a flow of an image display process (4) according to a fourth embodiment.

In the fourth embodiment, the CPU 101 performs an image display process (4) shown in FIG. 11. When the GUI 33 or the mouse pointer 36 is used to designate a position on a blood vessel in the coronary artery region A, the CPU 101 simultaneously designates a position on each blood vessel corresponding to the designated position, forms vertical tomographic images of the blood vessels at each designated position, and displays the vertical tomographic images. In addition, the CPU 101 measures and evaluates blood vessel luminal areas 391, 392, and 393 in the formed vertical tomographic images, and displays the blood vessel luminal areas 391, 392, and 393 such that an abnormal part is emphasized (see FIG. 12).

Next, the operation of the image processing device 100 according to the fourth embodiment will be described with reference to FIGS. 11 and 12.

The CPU 101 of the image processing device 100 according to the fourth embodiment reads a program and data related to the image display process (4) shown in FIG. 11 from the main memory 102 and performs the image display process (4) on the basis of the program and data.

In the image display process (4), first, the CPU 101 of the image processing device 100 reads three-dimensional image data from the storage device 103, similarly to the process from Step S101 to Step S104 in the first embodiment (Step S401). Then, the CPU 101 extracts the coronary artery region A from the acquired three-dimensional image data and displays the coronary artery region A in the entire image display region 31 of the display apparatus 107 (Step S402). In addition, the CPU 101 calculates the cores 41, 42, and 43 passing through the vicinities of the centers of the blood vessels A1, A2, and A3 from the coronary artery region A (Step S403). Then, the CPU 101 calculates the lengths R, L1, and L2 of the blood vessels from a branch portion to the deepest portion for the acquired cores 41, 42, and 43 and normalizes the calculated lengths R, L1, and L2 of the blood vessels (Step S404).

In Step S405 of FIG. 11, when the operator operates the mouse 108 to designate a position on the blood vessel or a distance from a starting position with, for example, the GUI 33 described in the first embodiment or the mouse pointer 36 described in the second embodiment (Step S405), the CPU 101 reads information of the designated position or distance (Step S406). In addition, the CPU 101 calculates corresponding positions of all of the blood vessels on the basis of the information of the designated position or distance. Then, the CPU 101 displays the lines 35a, 35b, and 35c indicating the designated position or the corresponding positions on the blood vessels A1, A2, and A3 of the coronary artery region A displayed in the entire image display region 31, respectively (Step S407). The designated position or the corresponding positions are calculated by the same method as that in the first embodiment or the second embodiment and thus a description thereof will be omitted.

In addition, the CPU 101 forms the vertical tomographic images 321, 322, and 323 of regions including the designated position and the corresponding positions in the blood vessels A1, A2, and A3 (Step S408).

The CPU 101 measures and evaluates blood vessel luminal areas in the vertical tomographic images 321, 322, and 323 (Step S409). The blood vessel luminal area is acquired by calculating an area of an imaged region which has a signal value equal to or more than a predetermined signal value (a CT value or a brightness value). The CPU 101 displays the vertical tomographic images 321, 322, and 323 in the detailed image display region 32 and emphasizes the vertical tomographic image having an abnormal part where, for example, the blood vessel luminal area is less than a reference blood vessel luminal area (Step S410).

Examples of the emphasized display include an enlarged display or a superimposed display of color maps which are color-coded for each signal value.

Figure 12:
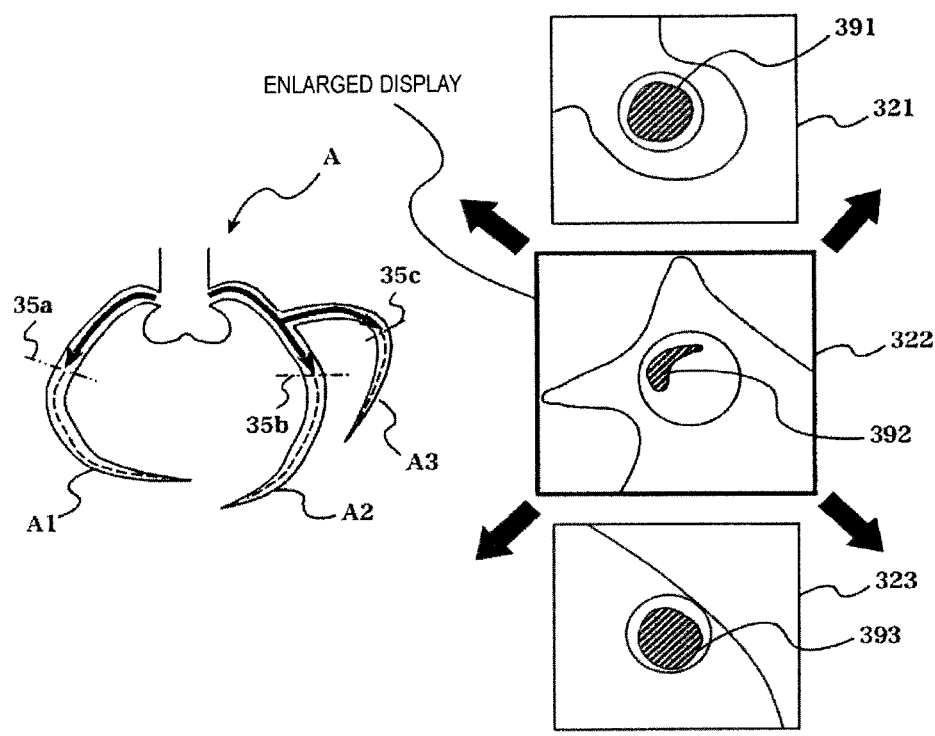
FIG. 12 is a diagram illustrating a display example according to the fourth embodiment.

As shown in FIG. 12, the blood vessel luminal areas 391, 392, and 393 of the vertical tomographic images 321, 322, and 323 displayed in the detailed image display region 32 are evaluated. When there is an abnormal part in any of the vertical tomographic images, the vertical tomographic image is displayed so as to be emphasized. In the example shown in FIG. 12, the vertical tomographic image 322 is enlarged and displayed.

In the process from Step S405 to Step S410, whenever an arbitrary position on a blood vessel is designated, positions (corresponding positions) on the other blood vessels corresponding to the designated position are calculated and the vertical tomographic images 321, 322, and 323 at the designated position and the corresponding positions are formed and displayed.

In addition, the blood vessel luminal areas are evaluated. When there is an abnormal part in any of the vertical tomographic images, the vertical tomographic image is displayed so as to be emphasized.

As described above, the image processing device 100 according to the fourth embodiment evaluates the blood vessel luminal areas in the vertical tomographic images 321, 322, and 323 displayed in the detailed image display region 32 and displays the vertical tomographic image having an abnormal part so as to be emphasized.

Therefore, the operator can easily determine the occurrence of an abnormality, such as the stenosis of blood vessels, which is helpful for diagnosis.

Fifth Embodiment

Next, an image process system 1 according to a fifth embodiment will be described. The hardware structure of the image process system 1 according to the fifth embodiment is the same as that of the image process system 1 according to the first embodiment shown in FIG. 1 and thus a description thereof will be omitted. In the fifth embodiment, the same components as those in the first embodiment are denoted by the same reference numerals.

Figure 13:
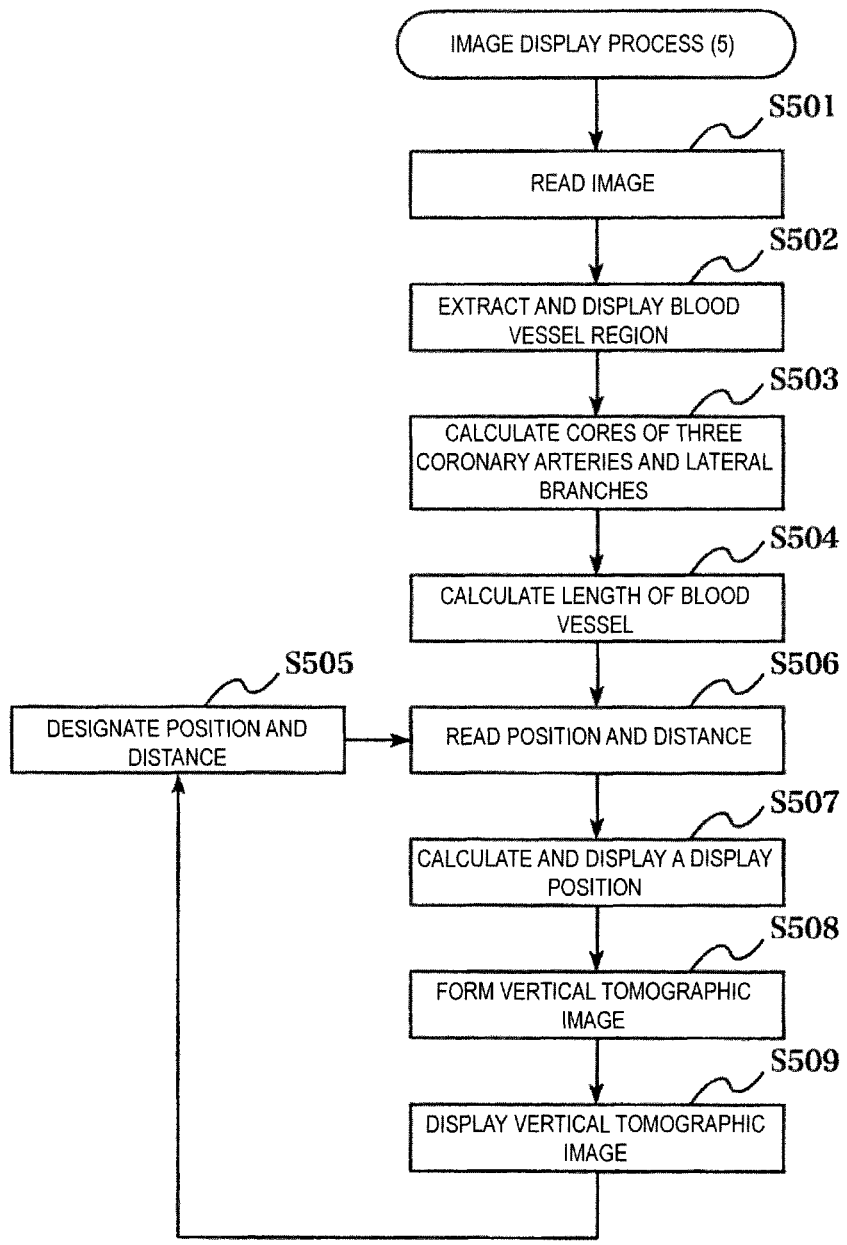
FIG. 13 is a flowchart illustrating a flow of an image display process (5) according to a fifth embodiment.

In the fifth embodiment, the CPU 101 performs an image display process (5) shown in FIG. 13 and performs extractions of cores and calculation of lengths of blood vessels for lateral branches in addition to the three coronary arteries. When the GUI 33 or the mouse pointer 36 is operated to designate an arbitrary position of any one of the blood vessels in the coronary artery region A, the CPU 101 calculates positions on the other blood vessels corresponding to the designated position, forms vertical tomographic images of the blood vessels at the designated position and the corresponding positions, and displays the vertical tomographic images.

Next, the operation of the image processing device 100 according to the fifth embodiment will be described with reference to FIGS. 13 to 15.

The CPU 101 of the image processing device 100 according to the fifth embodiment reads a program and data related to the image display process (5) shown in FIG. 13 from the main memory 102 and performs the image display process (5) on the basis of the program and data.

In the image display process (5), first, the CPU 101 of the image processing device 100 reads three-dimensional image data from the storage device 103 (Step S501). Then, the CPU 101 extracts the coronary artery region A from the acquired three-dimensional image data and displays the coronary artery region A in the entire image display region 31 of the display apparatus 107 (Step S502). In addition, the CPU 101 calculates cores of the three coronary arteries A1, A2, and A3 and lateral branches A11 to A15, A21 to A26, and A31 to A33 thereof from the coronary artery region A (Step S503). Then, the CPU 101 calculates length of each blood vessel from a branch portion to the deepest portion for each of the acquired cores. For the length of the lateral branch, the CPU 101 calculates a distance from a branch portion of each of the coronary arteries A1, A2, and A3 including the lateral branches to a branch point of the lateral branch and a distance from the branch point to the deepest portion of the lateral branch. The CPU 101 normalizes the calculated lengths of the blood vessels (Step S504).

Then, in Step S505 shown in FIG. 13, when the operator operates the mouse 108 to designate a position on the blood vessel or a distance from a starting position with, for example, the GUI 33 described in the first embodiment or the mouse pointer 36 described in the second embodiment (Step S505), the CPU 101 reads information of the designated position or distance (Step S506). In addition, the CPU 101 calculates corresponding positions of the three coronary arteries on the basis of the information of the designated position or distance, similarly to the first or second embodiment. For corresponding positions of the lateral branches, when the designated position or distance reaches the distance from the branch portion of each of the coronary arteries A1, A2, and A3 including the lateral branches to the branch point of the lateral branch, the CPU 101 calculates the corresponding position before the branch point of the lateral branch.

Then, the CPU 101 displays lines indicating the designated position or the corresponding positions on each blood vessel in the coronary artery region A (Step S507).

In addition, the CPU 101 forms a vertical tomographic image of each blood vessel at the designated position or the corresponding positions and displays the vertical tomographic images in the detailed image display region 32 (Steps S508 and 509). The vertical tomographic images of the lateral branches as well as the vertical tomographic images of the coronary arteries are displayed.

Figure 14:
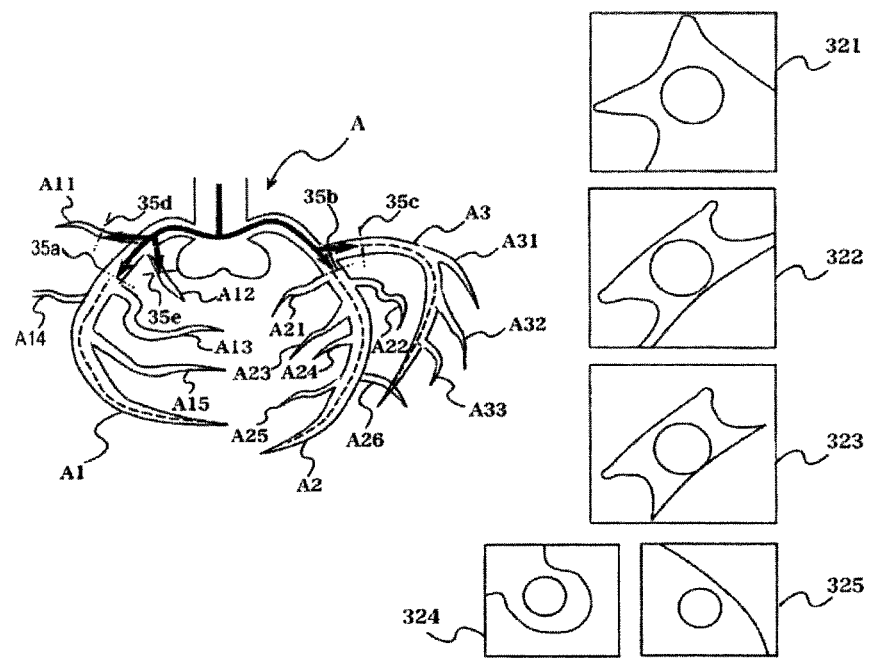
FIG. 14 is a diagram illustrating a display example according to the fifth embodiment.
Figure 15:
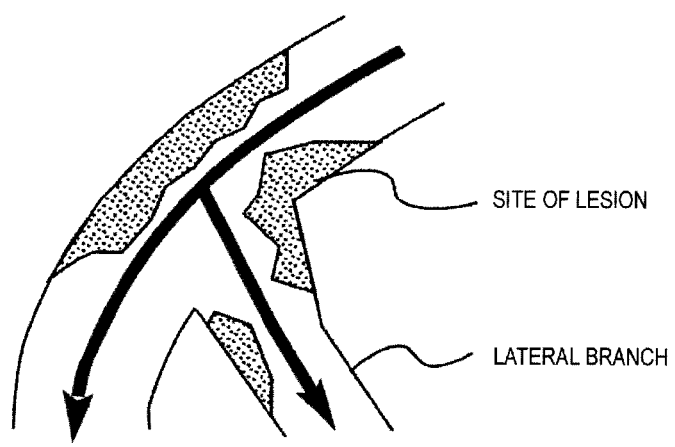
FIG. 15 is a diagram illustrating a site of a lesion of a lateral branch.

FIG. 14 shows a display state of the display apparatus 107 of the image processing device 100 at this stage.

As shown in FIG. 14, when an arbitrary position on a blood vessel or a distance from the starting point is designated, positions on the blood vessels A1, A2, and A3 of the coronary artery region A corresponding to the designated position or distance or corresponding positions of the lateral branches A11 and A12 are calculated, and lines 35*a*, 35*b*, 35*c*, 35*d*, and 35*e* are displayed at the corresponding positions and the designated position. In addition, the vertical tomographic images 321, 322, 323, 324, and 325 of the blood vessels A1, A2, A3, A11, and A12 at the corresponding positions and the designated position are formed and displayed in the detailed image display region 32.

In Step S509, when a plurality of the vertical tomographic images are displayed, the vertical tomographic images 321, 322, and 323 of the three main coronary arteries may be displayed with a large size and the vertical tomographic images 324 and 325 of the lateral branches may be displayed with a small size. In addition, the size of the vertical tomographic images may be determined by the thickness of the blood vessel. That is, the vertical tomographic image of an upstream portion (a portion close to the branch portion) of the blood vessel may be displayed with a size larger than that of a downstream portion (a portion close to the leading end). As such, when the size of the vertical tomographic images varies depending on a part of the blood vessel, it is easy for the operator to observe an important blood vessel (the main coronary artery or the upstream blood vessel) even when the plurality of vertical tomographic images are displayed on the same screen.

In the process from Step S505 to Step S509, whenever an arbitrary position on a blood vessel is designated, positions (corresponding positions) on the other blood vessels corresponding to the designated position are calculated and the detailed images (for example, the vertical tomographic images) of the three coronary arteries or the lateral branches at the designated position and the corresponding positions are formed and displayed.

As described above, in the image processing device 100 according to the fifth embodiment, for example, when the GUI 33 or the mouse pointer 36 is operated to designate an arbitrary position on a plurality of displayed blood vessels or a distance from the starting point, the CPU 101 calculates positions on the blood vessels (including coronary arteries and lateral branches) corresponding to the designated position, forms detailed images (for example, vertical tomographic images) at the designated position and the calculated corresponding positions, and displays the detailed images on the same display screen.

Therefore, the operator can view the detailed images of the lateral branches in addition to observing the three main coronary arteries, without changing a selection of the blood vessels. Therefore, observation can be easily performed, for example, regarding a branch point of the lateral branch or a site of a lesion in the lateral branch shown in FIG. 15.

Sixth Embodiment

Next, an image process system 1 according to a sixth embodiment will be described. The hardware structure of the image process system 1 according to the sixth embodiment is the same as that of the image process system 1 according to the first embodiment shown in FIG. 1 and thus a description thereof will be omitted. In the sixth embodiment, the same components as those in the first embodiment are denoted by the same reference numerals.

Figure 16:
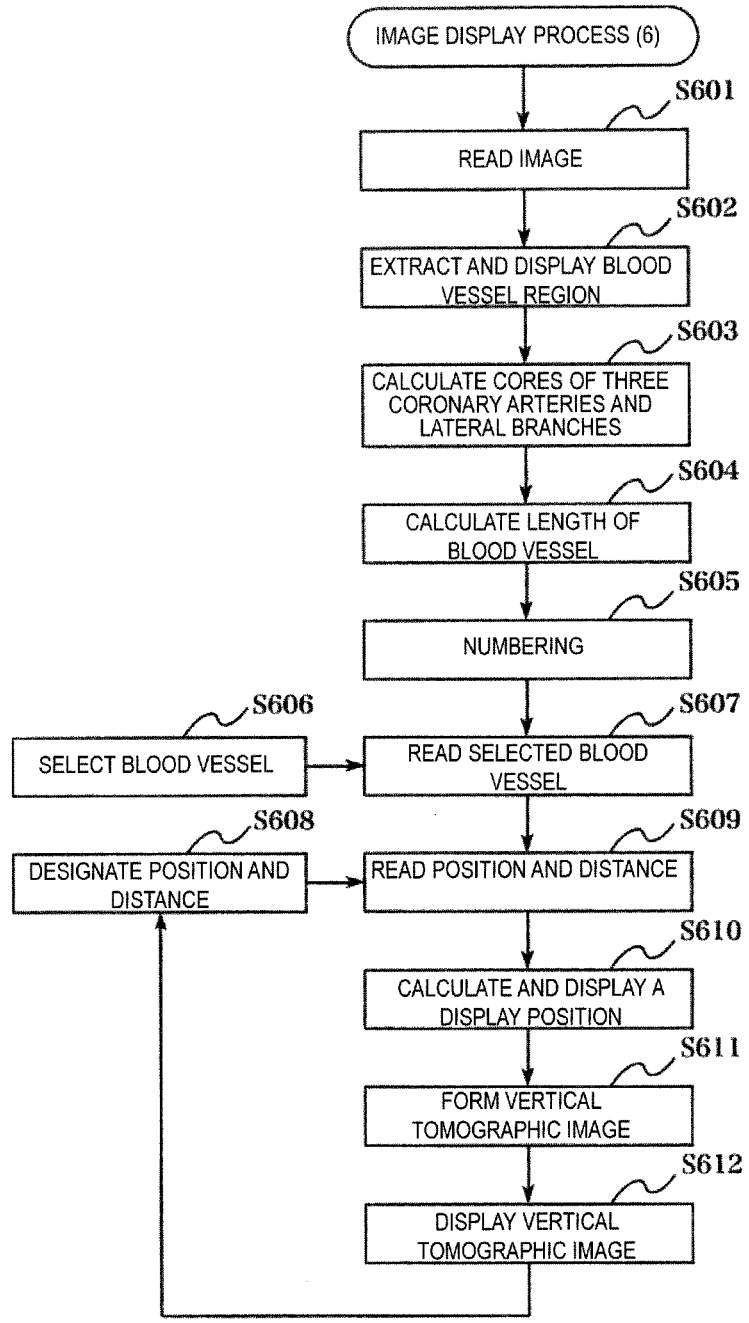
FIG. 16 is a flowchart illustrating a flow of an image display process (6) according to a sixth embodiment.

In the sixth embodiment, the CPU 101 performs an image display process (6) shown in FIG. 16. When the mouse pointer 36 is used to select arbitrary positions on a plurality of blood vessels in the coronary artery region A, the CPU 101 forms each detailed image (for example, a vertical tomographic image) of the blood vessel at the selected position and displays the detailed image.

Next, the operation of the image processing device 100 according to the sixth embodiment will be described with reference to FIGS. 16 and 17.

The CPU 101 of the image processing device 100 according to the sixth embodiment reads a program and data related to the image display process (6) shown in FIG. 16 from the main memory 102 and performs the image display process (6) on the basis of the program and data.

In the image display process (6), first, the CPU 101 of the image processing device 100 reads three-dimensional image data from the storage device 103, similarly to the process from Step S501 to Step S504 in the fifth embodiment (Step S601). Then, the CPU 101 extracts the coronary artery region A from the acquired three-dimensional image data and displays the coronary artery region A in the entire image display region 31 of the display apparatus 107 (Step S602). In addition, the CPU 101 calculates cores passing through the vicinities of the centers of three coronary arteries and lateral branches from the coronary artery region A (Step S603). Then, the CPU 101 calculates the length of each blood vessel from a branch portion to the deepest portion for the acquired cores. For the lengths of the lateral branches, the CPU 101 calculates a distance from a branch point to the deepest portion of the blood vessel, unlike the fifth embodiment. The CPU 101 normalizes the calculated lengths of the blood vessels (Step S604).

The CPU 101 numbers (gives numbers to) all of the blood vessels from which the cores are extracted (Step S605). The CPU 101 stores the numbered blood vessels in the main memory 102 so as to be associated with numbers to which information of positions or the lengths of the blood vessels are added.

Then, in Step S606 of FIG. 16, first, when the operator operates the mouse to select arbitrary blood vessels, the CPU 101 searches for, for example, information of the cores or the information of the lengths of the blood vessels using the numbers given to the selected blood vessels as a key and reads the information (Step S607). In this case, as shown in FIG. 17, the selected blood vessels may be displayed so as to be identified.

Then, for example, when the mouse pointer 36 is used to designate positions on the selected blood vessels or a distance from a starting point of each of the selected blood vessels (Step S608), the CPU 101 reads information of the designated positions or distances (Step S609). Then, the CPU 101 displays lines 51a, 51b, and 51c at the designated positions of the selected blood vessels (Step S610). Then, the CPU 101 forms detailed images, such as vertical tomographic images 511, 512, and 513, at the designated positions and displays the detailed images in the detailed image display region 32 (Steps S611 and 612).

In the process from Step S607 to Step S612, whenever, an arbitrary blood vessel is selected and a position is designated, the CPU 101 displays the line at the designated position, forms the vertical tomographic image, and displays the vertical tomographic image in the detailed image display region 32. Any number of blood vessels may be selected, and the upper limit of the number of blood vessels may be set in a range in which the blood vessels can be displayed on the display screen. Similarly to the fifth embodiment, the CPU 101 may display the vertical tomographic images of the three main coronary arteries with a large size and display the vertical tomographic images of the lateral branches with a small size. The size of the detailed image may be determined by the thickness of the blood vessel. That is, the vertical tomographic image of an upstream portion of the blood vessel may be displayed with a size larger than that of a downstream portion of the blood vessel.

Figure 17:
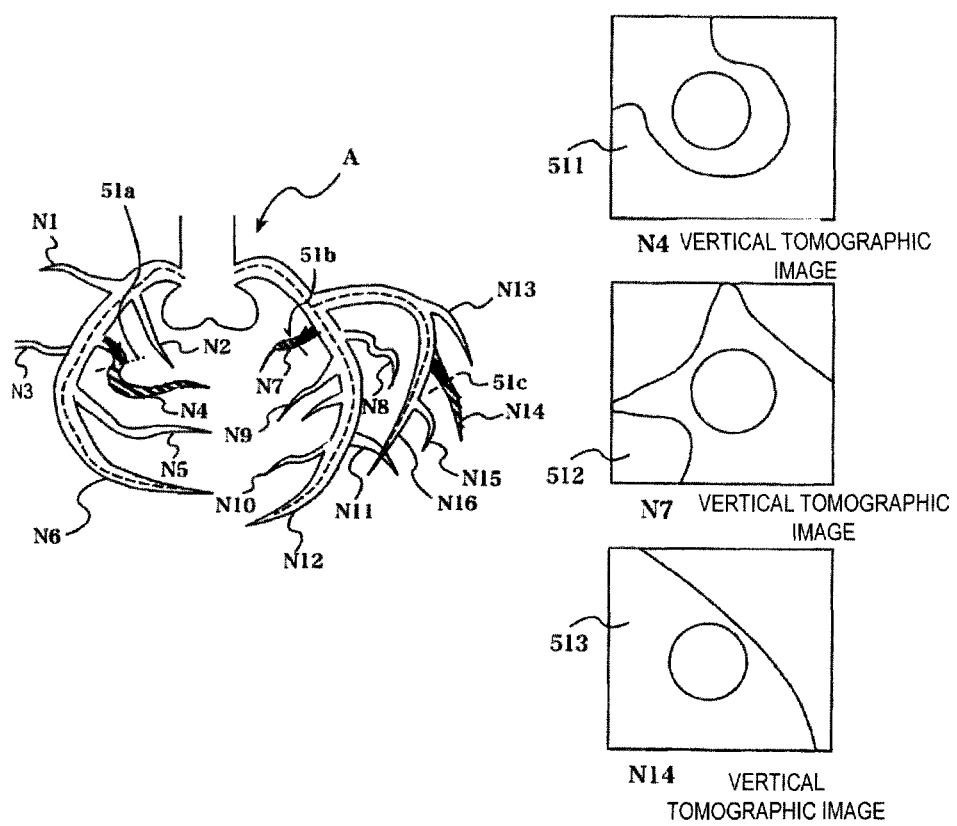
FIG. 17 is a diagram illustrating a display example according to the sixth embodiment.

As shown in FIG. 17, for example, when blood vessels N4, N7, and N14 are selected and arbitrary positions on the selected blood vessels N4, N7, and N14 are designated, the lines 51a, 51b, and 51c are displayed at the designated positions. In addition, the vertical tomographic images 511, 512, and 513 of the blood vessels N4, N7, and N14 at the designated positions are formed and displayed in the detailed image display region 32.

As described above, in the image processing device 100 according to the sixth embodiment, when arbitrary blood vessels are selected from a plurality of displayed blood vessels and positions on the selected blood vessels are designated, the CPU 101 forms detailed images of the blood vessels corresponding to the designated positions and displays the detailed images in the detailed image display region 32.

Therefore, the operator can select only a plurality of blood vessels desired to be observed from the coronary artery region A and observe the vertical tomographic images at the same time. Therefore, the operator can quickly observe the blood vessels.

The image processing devices according to the exemplary embodiments of the invention have been described above, but the invention is not limited to the above-described embodiments. For example, the methods according to the first to sixth embodiments may be appropriately combined with each other. It will be apparent to those skilled in the art that various modifications and changes can be made without departing from the scope and spirit of the invention. Therefore, it should be understood that the modifications and changes are also included in the technical scope of the invention.

DESCRIPTION OF REFERENCE NUMERALS

1: IMAGE PROCESS SYSTEM
100: IMAGE PROCESSING DEVICE
101: CPU
102: MAIN MEMORY
103: STORAGE DEVICE
104: COMMUNICATION I/F
105: DISPLAY MEMORY
106: I/F
107: DISPLAY DEVICE
108: MOUSE (EXTERNAL APPARATUS)
109: INPUT DEVICE
110: NETWORK

111: IMAGE DATABASE
112: MEDICAL IMAGING APPARATUS
A: CORONARY ARTERY REGION
A1: RIGHT CORONARY ARTERY
A2: LEFT ANTERIOR DESCENDING CORONARY ARTERY
A3: LEFT CIRCUMFLEX CORONARY ARTERY
32: DETAILED IMAGE DISPLAY REGION
33: GUI
41, 42, 43: CORE

The invention claimed is:

1. An image processing device comprising:
   display region forming means configured to form a first region in which an entire image of a structure divided into a plurality of branches is displayed and a second region in which detailed images of the plurality of different branches included in the entire image are displayed on the same display screen;
   designating means configured to designate a position on a first branch amongst the plurality of different branches and to calculate another position on another branch other than the first branch, wherein the calculated position on said another branch corresponds in a length direction to the designated position on the first branch, wherein the calculated position is based on a ratio of a first length from a start of the first branch to the designated position on the first branch and a second length from the start of the first branch to a deepest point on the first branch; and
   display means configured to form the detailed image of each branch to be displayed on a basis of each position designated and calculated by the designating means and displaying each detailed image in the second region.

2. The image processing device according to claim 1, further comprising:
   GUI display means configured to generate a GUI for designating the position of the branch in a length direction and displaying the GUI,
   wherein, when the GUI generated by the GUI display means is operated to designate an arbitrary position on the GUI, the designating means calculates a position on each branch to be displayed which corresponds to the designated position on the GUI, and
   the display means displays the detailed image of each branch at the position calculated by the designating means in the second region.

3. The image processing device according to claim 1,
   wherein, when a pointer displayed on the entire image is operated to input an instruction to designate an arbitrary position on any branch in the entire image, the designating means calculates positions, which correspond to the position designated by the input instruction, on branches other than the branch designated by the input instruction among the branches to be displayed, and
   the display means displays the detailed image of each branch at the position designated by the input instruction or the positions calculated by the designating means in the second region.

4. The image processing device according to claim 1,
   wherein the detailed image displayed in the second region is a tomographic Image orthogonal to a core of each branch or a three-dimensional perspective projection image.

5. The image processing device according to claim 1, further comprising: detecting means configured to detect an abnormal part on the basis of the detailed image, wherein the display means displays the detailed image from which the abnormal part is detected by the detecting means so as to be emphasized.

6. The image processing device according to claim 1,
   wherein the display means displays each of the detailed image in the second region such that the size of the detailed image of a main branch or a part of each branch close to a branch portion is larger than that of a lateral branch or a part of the branch close to a leading end.

7. The image processing device according to claim 1,
   wherein, when the entire image displayed in the first region includes three coronary arteries, the three coronary arteries are display targets in the second region.

8. An image processing method comprising:
   a display region forming step of forming a first region in which an entire image of a structure divided into a plurality of branches is displayed and a second region in which detailed images of the plurality of different branches included in the entire image are displayed on the same display screen;
   a designating step of designating a position on a first branch amongst the plurality of different branches and to calculate another position on another branch other than the first branch, wherein the calculated position on said another branch corresponds in a length direction to the designated position on the first branch, wherein the calculated position is based on a ratio of a first length from a start of the first branch to the designated position on the first branch and a second length from the start of the first branch to a deepest point on the first branch; and
   a display step of forming the detailed image of each branch to be displayed on a basis of each position designated and calculated by the designating step and displaying each detailed image in the second region.

* * * * *